US011679928B2

(12) United States Patent
Mosler et al.

(10) Patent No.: US 11,679,928 B2
(45) Date of Patent: *Jun. 20, 2023

(54) VAPOCOOLANT DEVICE

(71) Applicant: 623 Medical, LLC, Morrisville, NC (US)

(72) Inventors: Theodore J. Mosler, Morrisville, NC (US); Eli Nichols, Morrisville, NC (US); Charles McCall, Morrisville, NC (US); Andrew Corson, Morrisville, NC (US); James Fentress, Morrisville, NC (US)

(73) Assignee: 623 MEDICAL, LLC, Morrisville, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/826,679

(22) Filed: May 27, 2022

(65) Prior Publication Data

US 2022/0356002 A1 Nov. 10, 2022

Related U.S. Application Data

(63) Continuation of application No. 17/295,350, filed as application No. PCT/US2020/059475 on Nov. 6, 2020, now Pat. No. 11,352,196.

(60) Provisional application No. 62/932,144, filed on Nov. 7, 2019.

(51) Int. Cl.
*B65D 83/38* (2006.01)
*B65D 83/14* (2006.01)
*A61F 7/00* (2006.01)

(52) U.S. Cl.
CPC ......... *B65D 83/386* (2013.01); *B65D 83/752* (2013.01); *B65D 83/757* (2013.01); *B65D 83/7538* (2013.01); *A61F 7/00* (2013.01)

(58) Field of Classification Search
CPC ............... B65D 83/386; B65D 83/752; B65D 83/7538; B65D 83/757; B65D 83/205; B65D 83/207; B65D 83/384; B65D 83/40; A61F 7/00; A61L 2/08–12
USPC ........................................................ 222/173
See application file for complete search history.

(56) References Cited

U.S. PATENT DOCUMENTS

| 2,940,641 A | 6/1960 | Norrish |
| 2,966,283 A | 12/1960 | Darvie |
| 3,080,989 A | 3/1963 | Ramsbotham |
| 3,262,607 A | 7/1966 | Hirsch |
| 3,272,391 A | 9/1966 | Meshberg |

(Continued)

FOREIGN PATENT DOCUMENTS

GB 1331329 A 9/1973

OTHER PUBLICATIONS

USPTO; International Search Report and Written Opinion for International Application No. PCT/US2020/059475 dated Feb. 4, 2021, 11 Pages.

*Primary Examiner* — Paul R Durand
*Assistant Examiner* — Michael J. Melaragno
(74) *Attorney, Agent, or Firm* — Christopher J. Knors; Moore & Van Allen PLLC

(57) ABSTRACT

The present disclosure discloses and describes a vapocoolant dispenser. Specifically, the dispenser comprises a housing and container of vapocoolant, the dispenser configured to receive a sterilizable dose of high energy radiation and to provide a sterile, hermetically sealed vapocoolant dispenser.

10 Claims, 16 Drawing Sheets

(56) References Cited

U.S. PATENT DOCUMENTS

| | | | |
|---|---|---|---|
| 3,272,392 | A | 9/1966 | Meshberg |
| 4,981,679 | A | 1/1991 | Briggs et al. |
| 5,060,823 | A | 10/1991 | Perlman |
| 5,219,005 | A | 6/1993 | Stoffel |
| 5,772,083 | A | 6/1998 | Joulia |
| 6,123,900 | A | 9/2000 | Vellutato |
| 10,479,592 | B1 | 11/2019 | Caruso |
| 10,661,973 | B1 | 5/2020 | Caruso |
| 11,352,196 | B2 * | 6/2022 | Mosler ................ B65D 83/757 |
| 2003/0206825 | A1 | 11/2003 | Vellutato |
| 2005/0035154 | A1 | 2/2005 | Meshberg |
| 2012/0187151 | A1 | 7/2012 | DeJonge |
| 2014/0373973 | A1 | 12/2014 | Windmiller |
| 2017/0354807 | A1 | 12/2017 | Lozevski |
| 2018/0008509 | A1 | 1/2018 | Ho |
| 2020/0039732 | A1 | 2/2020 | Ditto et al. |
| 2020/0100934 | A1 | 4/2020 | Ariano et al. |
| 2020/0146739 | A1 | 5/2020 | Klever et al. |

* cited by examiner

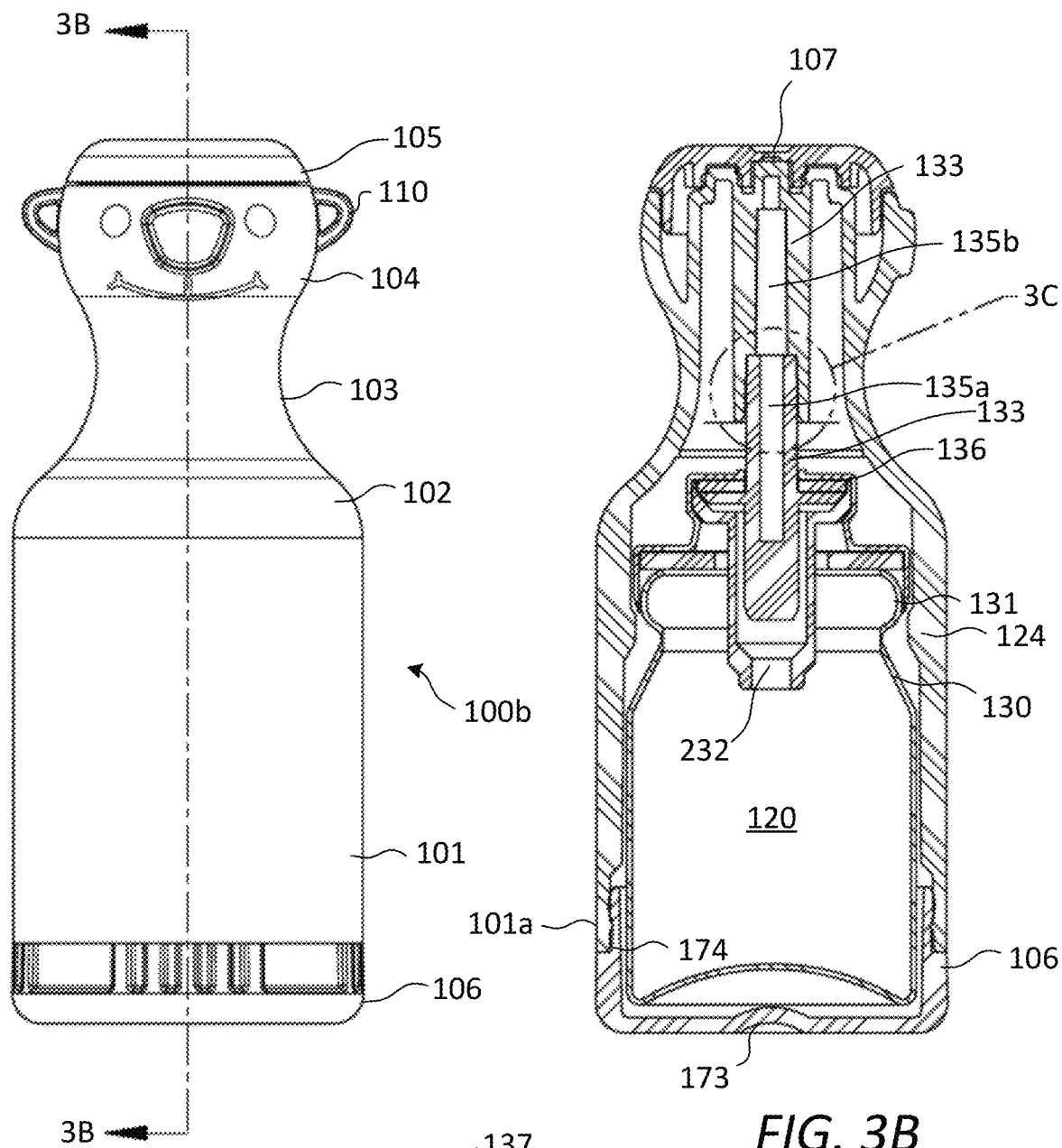
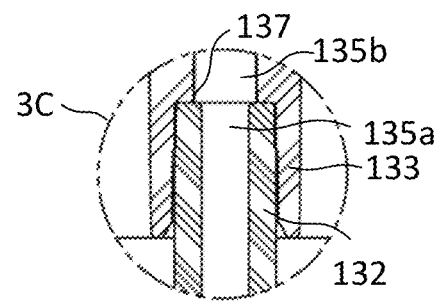
FIG. 3A
FIG. 3B
FIG. 3C

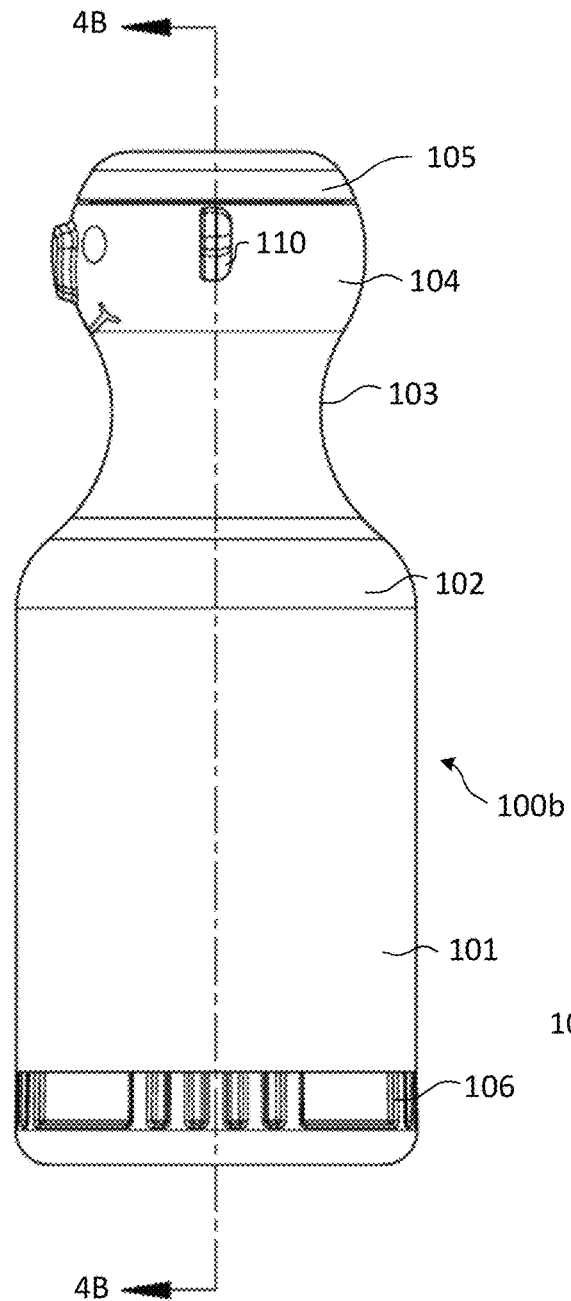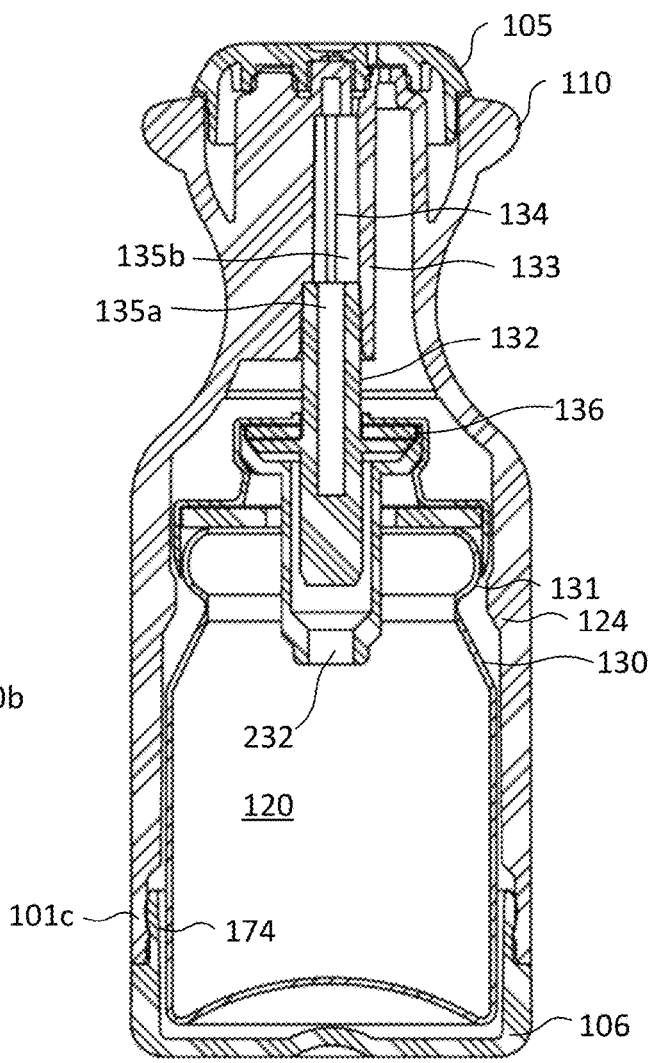
FIG. 4A
FIG. 4B

VAPOCOOLANT DEVICE

CROSS-REFERENCE TO RELATED APPLICATIONS

This application is a Continuation of U.S. application Ser. No. 17/295,350, filed May 19, 2021, which is a 35 U.S.C. § 371 National Stage Application of International Application No. PCT/US20/59475, filed Nov. 6, 2020, which claims the benefit of U.S. Provisional Application No. 62/932,144 filed on Nov. 7, 2019, the entirety of each of which is incorporated herein by reference.

TECHNICAL FIELD

The present disclosure relates to a vapocoolant dispenser suitable for sterilization. Specifically, the vapocoolant dispenser comprises a housing, the housing comprising a vapocoolant container, the housing and vapocoolant container configured for release of sterilized vapocoolant.

BACKGROUND

Injections are employed millions of times daily all over the world to deliver medicines into people as well as animals. Many times, injections are made in areas of the body that are sensitive to pain as the needle is inserted. Cooling of the skin in the vicinity of injection site using vapocoolant is known to reduce pain, but existing dispensing techniques and devices can be cumbersome to employ, may cause injury to the injection site, and employ flammable or environmentally unfriendly materials. Recently, products designed for dispensing vapocoolants have been found to contain or be contaminated with microorganisms, leading to recalls and other issues.

SUMMARY

In a first example, a sterilizable vapocoolant dispenser is provided. The sterilizable vapocoolant dispenser comprising: a container comprising vapocoolant, the container having a valve member configured to release the vapocoolant; a housing having a distal open end; a proximal open end sized to receive a majority portion of the container and exposing the remainder portion of the container, and; a bottom cover sealing the proximal open end and the remainder portion of the container; a lid sealing the distal open end, the lid coupled to the valve member; and a nozzle receiving member positioned in the housing and configured to engage the valve member for releasing the vapocoolant. In one aspect, the container and its contents are configured for sterilization by high energy radiation.

In another aspect, the housing has an inward and outward tapered portion between the distal open end and the proximal open end for receiving fingers of a human hand.

In another aspect, alone or in combination with any of the previous aspects, the container is fixedly positioned in the housing. In another aspect, alone or in combination with any of the previous aspects, the lid is irreversibly sealed to the distal open end. In another aspect, alone or in combination with any of the previous aspects, the bottom cover is releasably coupled to the proximal open end.

In another example, a sterilized vapocoolant dispenser is provided. The sterilized vapocoolant dispenser comprising: a container comprising sterilized vapocoolant, the container having a valve member configured to release the vapocoolant; a housing having a distal open end; a proximal open end sized to receive a majority portion of the container and exposing the remainder portion of the container, and; a bottom cover sealing the proximal open end and the remainder portion of the container; a lid sealing the distal open end, the lid coupled to the valve member; and a nozzle receiving member positioned in the housing and configured to engage the valve member for releasing the vapocoolant. In one example, the container and vapocoolant are configured to remain sterilized until used.

In another aspect, alone or in combination with any of the previous aspects, the container is fixedly positioned in the housing. In another aspect, alone or in combination with any of the previous aspects, the lid is irreversibly sealed to the distal open end. In another aspect, alone or in combination with any of the previous aspects, the bottom cover is releasably coupled to the proximal open end.

In yet another example, a method of manufacturing a sterilized vapocoolant dispenser is provided, the method comprising: introducing a container containing vapocoolant to a housing, the housing comprising a distal open end, a proximal open end sized to receive a majority portion of the container and exposing the remainder portion of the container, and; hermetically sealing the proximal open end and the remainder portion of the container with a releasably sealed bottom cover; sealing the distal open end with a irreversibly sealed lid; and sterilizing the vapocoolant and housing simultaneously using high energy radiation.

These and other objects, aspects and features of the present disclosure will be better understood from the following detailed description of the preferred embodiment when read in conjunction with the appended drawing figures.

BRIEF DESCRIPTION OF THE DRAWINGS

FIG. 3A illustrates a front view of the dispenser of the dispenser of FIG. 1B.

FIG. 3B is a sectional view taken along line 3B-3B of the dispenser of FIG. 3A.

FIG. 3C is an enlarged view of section 3C of FIG. 3B.

FIG. 4A illustrates a side view of the dispenser of the dispenser of FIG. 1B.

FIG. 4B is a sectional view taken along line 4B-4B of the dispenser of FIG. 4A.

DETAILED DESCRIPTION

Figure 1A:
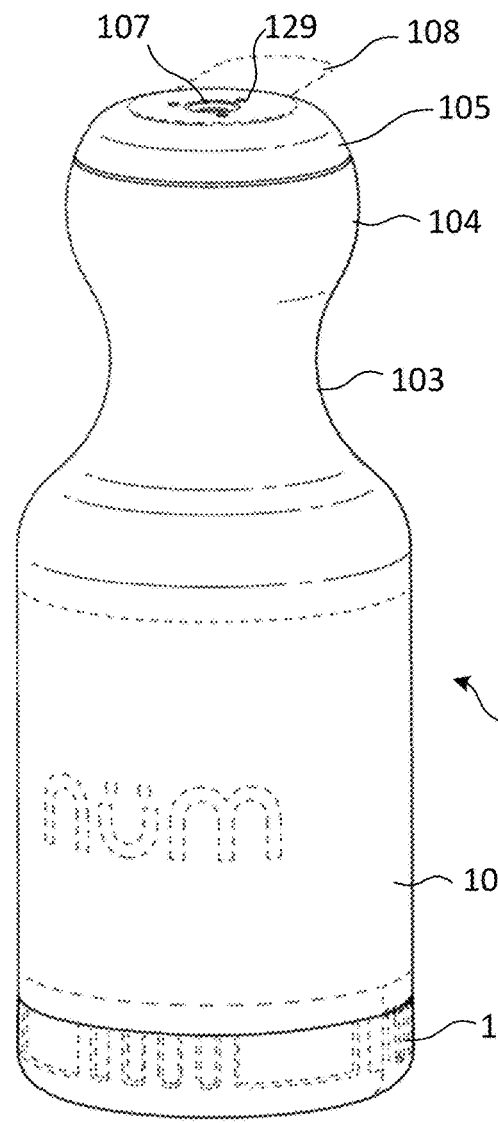
FIG. 1A illustrates a dispenser according to the present disclosure.

To address the technical problem of vapocoolant dispensing devices suffering from the delirious effects of microorganism contamination, the present disclosure provides a technical solution that provides a sterilizable and/or sterile vapocoolant dispenser and methods of manufacturing same. As disclosed herein, the dispenser is configured to hermetically receive and contain a vapocoolant container, be subject to high-energy radiation sterilization, and provide for dispensing of sterile vapocoolant. The dispenser disclosed herein is also configured for single use. The presently disclosed dispenser is designed to maintain a sterile fluid pathway until used. The presently disclosed dispenser does not require packaging in a sterile pouch or any other system designed to keep the entire device sterile, although, it is optionally configured to be packaged in such a manner.

As used in this disclosure, the term "sterile" is understood to mean, for example, a medical device that is free of viable microorganisms as determined by International standards that specify requirements including validation and routine control of sterilization processes, and require, when it is necessary to supply a sterile medical device, that adventitious microbiological contamination of a medical device prior to sterilization be minimized and/or reduced to a level as prescribed by one or more of the validation standards set by the International Standards Organization (ISO). Whereas, medical devices produced under standard manufacturing conditions in accordance with the requirements for quality management systems (see, for example, ISO 13485) may, prior to sterilization, have microorganisms on them, albeit in low numbers, such products are non-sterile. Thus, "sterile" as used herein is the result of sterilization sufficient to inactivate microbiological contaminants and thereby transform the non-sterile product into sterile product in accordance with the one or more ISO validation standards.

As used in this disclosure, the term "sterilizable" is understood to mean an article's or chemical's ability to substantially retain its chemical and physical properties and minimization or absence of transformations to or production of radiation-induced reaction products after receiving a sterilizable high energy radiation dose, such ability being maintained for period of time after receiving the high energy radiation dose. For example, a vapocoolant, after receiving a sterilizable high energy radiation dose would substantially or completely retain its chemical and physical properties with acceptably low or undetectable levels of radiation-induced reaction products for at least 6 months after receiving the high energy radiation dose. Likewise, a dispenser configured to hermetically seal a vapocoolant and its associated container, after receiving a sterilizable high energy radiation dose would substantially or completely retain its chemical and physical properties and provide for the maintaining of stability of the vapocoolant, for at least 6 months after exposure to the high energy radiation dose.

As used in this disclosure, the term "hermetically" is understood to mean completely sealed, so as to prevent or significantly reduce the escape or entry of air, moisture, microorganisms and other contamination directly or indirectly affecting sterility.

In one aspect, the present devices are intended for providing topical application of a vapocoolant to skin. By skin, it is intended to include the dermis and epidermis, intact mucous membranes, the oral cavity, nasal passageways and the lips. In one aspect, the present device is intended to provide pain management associated with injections, e.g., pre-injection anesthesia, including but not limited to venipuncture, IV starts, minor surgical procedures, vaccinations, pediatric care, and the temporary relief of pain from injuries, e.g., topical anesthesia, such as sprains, bruising, cuts, abrasions, and insect bites. The present device can also provide myofacial pain management. The dispenser can be configured to dispense other compositions, such as medicaments, dissolved or dispensed or distributed in such vapocoolants (e.g., low boiling solvents), such as ether or fluorocarbons, for non-invasive peroral (through the mouth), topical (skin), transmucosal (nasal, buccal/sublingual, vaginal, ocular and rectal) and inhalation dispensing to infants or adults. Other compositions that can be dispensed by the present dispenser can include removable or indelible inks, e.g., for tattooing or otherwise marking skin with indicia, e.g., phosphorescent inks.

Exemplary examples and discussions that now follow recite the use of a vapocoolant to describe manner and method of the presently disclosed dispenser. When the dispenser is employed with a vapocoolant, e.g., as a "vapocoolant dispenser," vapocoolant is released and caused to contact the skin, producing a rapid cooling effect upon contact. In one aspect, the dispenser is configured to provide the vapocoolant in the form of an aerosol, in either a mist or stream spray. Upon contact with the skin or mucosal membranes, the dispensed vapocoolant evaporates rapidly due to the low boiling point of the vapocoolant and the relatively high temperature associated with skin, causing a rapid cooling effect at the application site by the evaporation of the vapocoolant.

The container configured for containing the vapocoolant can be comprised of any material suitable for containing vapocoolant, which typically involves pressure slightly above that of atmospheric. Suitable materials include metals such as stainless steel and aluminum, plastics, reinforced plastics, glass, and ceramics.

In one portion of the housing one or more suitable structures are provided that receives the container and its associated valve member and renders the valve member substantially stationary in a first state. Longitudinal traversal of the container (along the longitudinal axis of the dispenser housing) causes the valve member to open so as to affect dispensing of the vapocoolant from within the container and to exit from the dispenser. The dispenser of the present disclosure is intended, in one variation, to be provided in a sterile condition or state and used continuously until the container is depleted of vapocoolant and then discarded. The device may be used multiple times and, even, on multiple patients. Of course, the device may be used solely with a single patient and discarded after such use.

The housing can be made of metal, glass, or ceramic. In one aspect, the housing and any or all of its components can be made of plastic, e.g., by any desired method including injection molding, compression molding, rotational molding, 3-D printing, and the like. The container can be of any material suitable for a vapocoolant, e.g., a plastic, metal, glass, or ceramic material capable of containing a liquid and/or gas at a pressure above atmospheric. The container can be sized to hold 0.1-1000 mL of vapocoolant. In one aspect, the container is sized to contain about 3.5 fl. oz. (103.5 mL). In other aspects, the container is sized to hold 0.5 mL, 1 mL, 2 mL, 5 mL, 10 mL, 25 mL, 50 mL, 75 mL, 200 mL, 500 mL, or 750 mL or more of vapocoolant.

The vapocoolant can be any liquid or combination of liquids having properties suitable for use as a vapocoolant. Such properties would include, low toxicity, low flammability and low combustibility, and/or includes materials having suitable boiling point and vapor pressure at typical or envisioned end-use temperature/pressure conditions. In one aspect, one or more halogenated hydrocarbons can be used as vapocoolants. In other aspects, suitable vapocoolants include one or more refrigerants as defined by American Society of Heating, Refrigerating and Air Conditioning Engineers (ASHRAE) as hydrochlorofluoroolefin, hydrochloric carbon hydrochloroolefin, hydrocarbon, hydroolefin, perfluorocarbon, perfluroolefin, perchlorocarbon, perchloroolefin, or mixtures thereof, for example, 1,1,1,3,3-pentafluoropropane, and 1,1,1,2-tetrafluoroethane mixture. One or more chemical compounds, e.g., medicaments, can be at least partially dispersed or dispensed or dissolved in the vapocoolant. In one aspect, the contents of the container, without pressurized air or inert gas, provides its own headspace pressure of above ambient atmospheric pressure, e.g., 1.01 to about 3 atmospheres at ambient temperature. For example, 1-3 atmospheres of pressure (about 15 psi to about 45 psi) is achievable by one or more vapocoolants or combinations of one or more vapocoolants and one or more hydrofluorocarbon alkanes (HFA), which can be safely contained in the container of the present disclosure. This head-space pressure without pressurized air or other gas is obtainable, for example, by providing a 95% mixture of a vapocoolant and a 5% mixture of a HFA, e.g., 95 wt. % of 1,1,1,3,3-Pentafluoropropane and 5 wt. % of 1,1,1,2-Tetrafluoroethane. Other combinations are possible to achieve the head-space pressure and encompassed by the present disclosure. Vapocoolants can include, without limitation, one or more non-halogen containing low boiling fluids suitable for topical skin application, provided that the non-halogen containing the fluid is capable of operating as a self-propellant by providing a suitable pressure for discharge in a vapor space above the liquid supply of the vapocoolant.

Figure 1B:
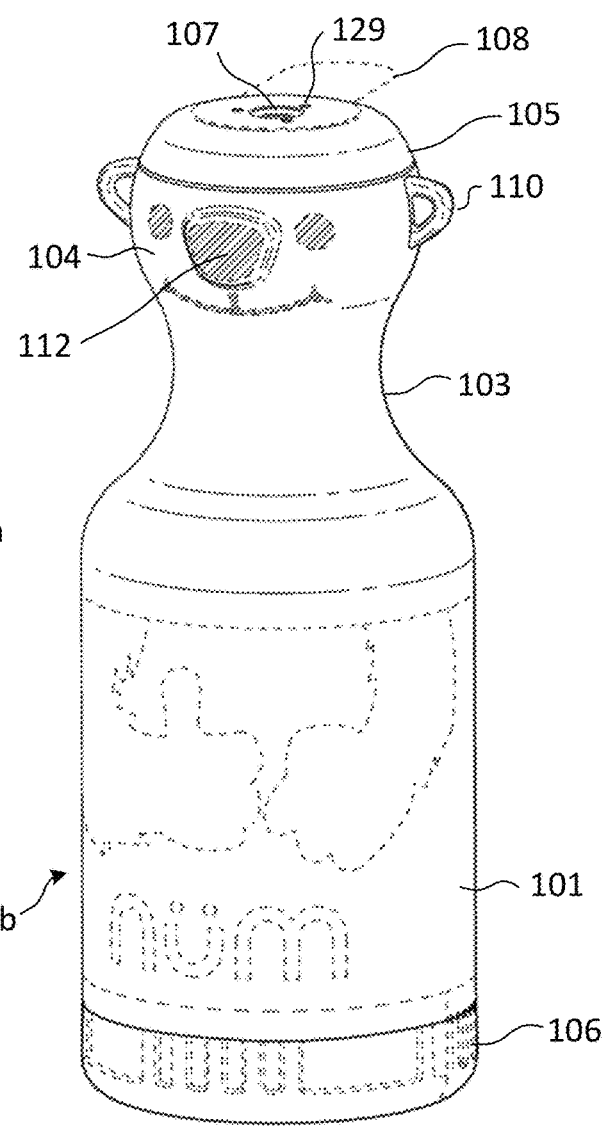
FIG. 1B illustrates an alternate dispenser according to the present disclosure.
Figure 2A:
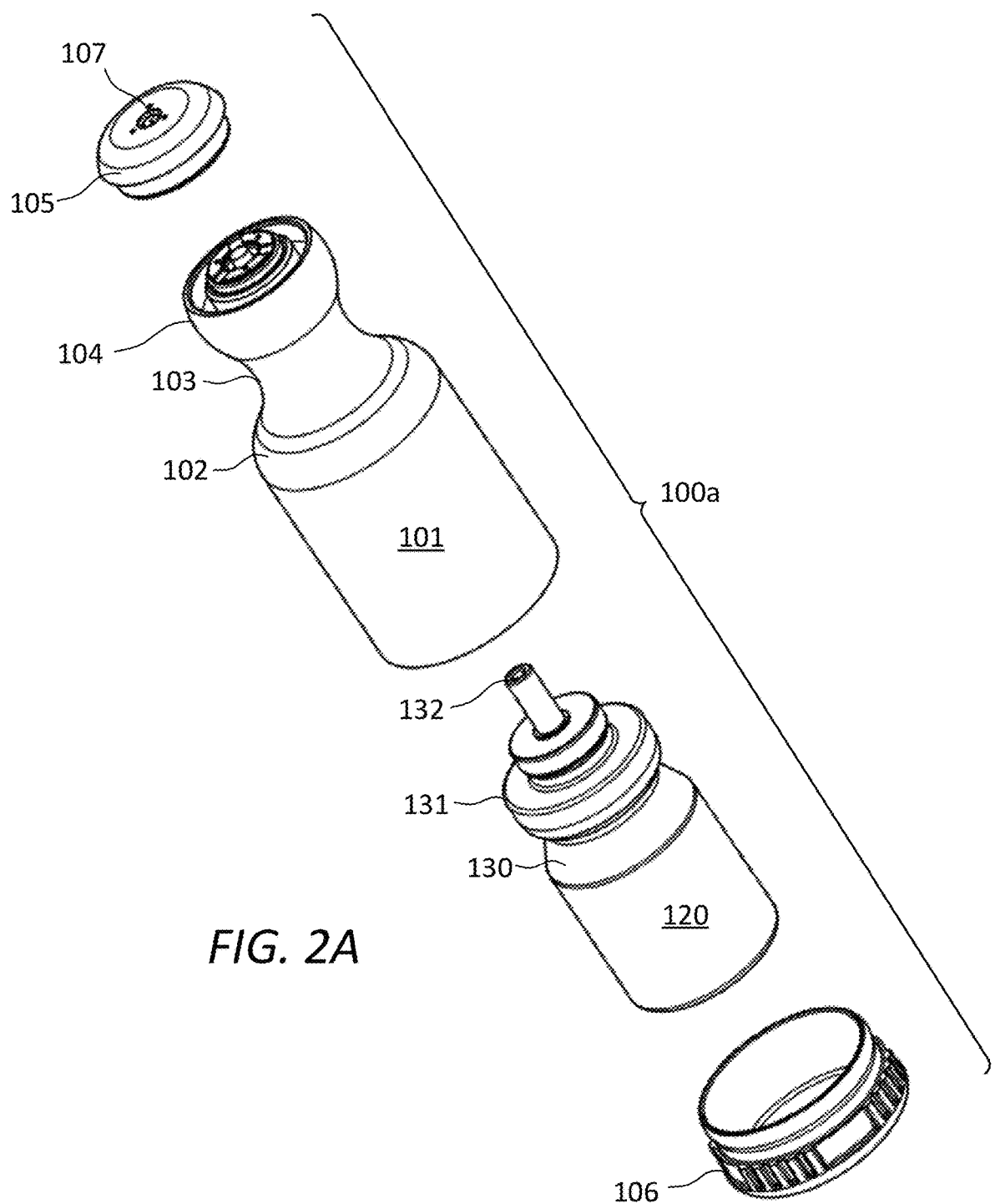
FIG. 2A illustrates an exploded view of the dispenser of FIG. 1A according to the present disclosure.
Figure 2B:
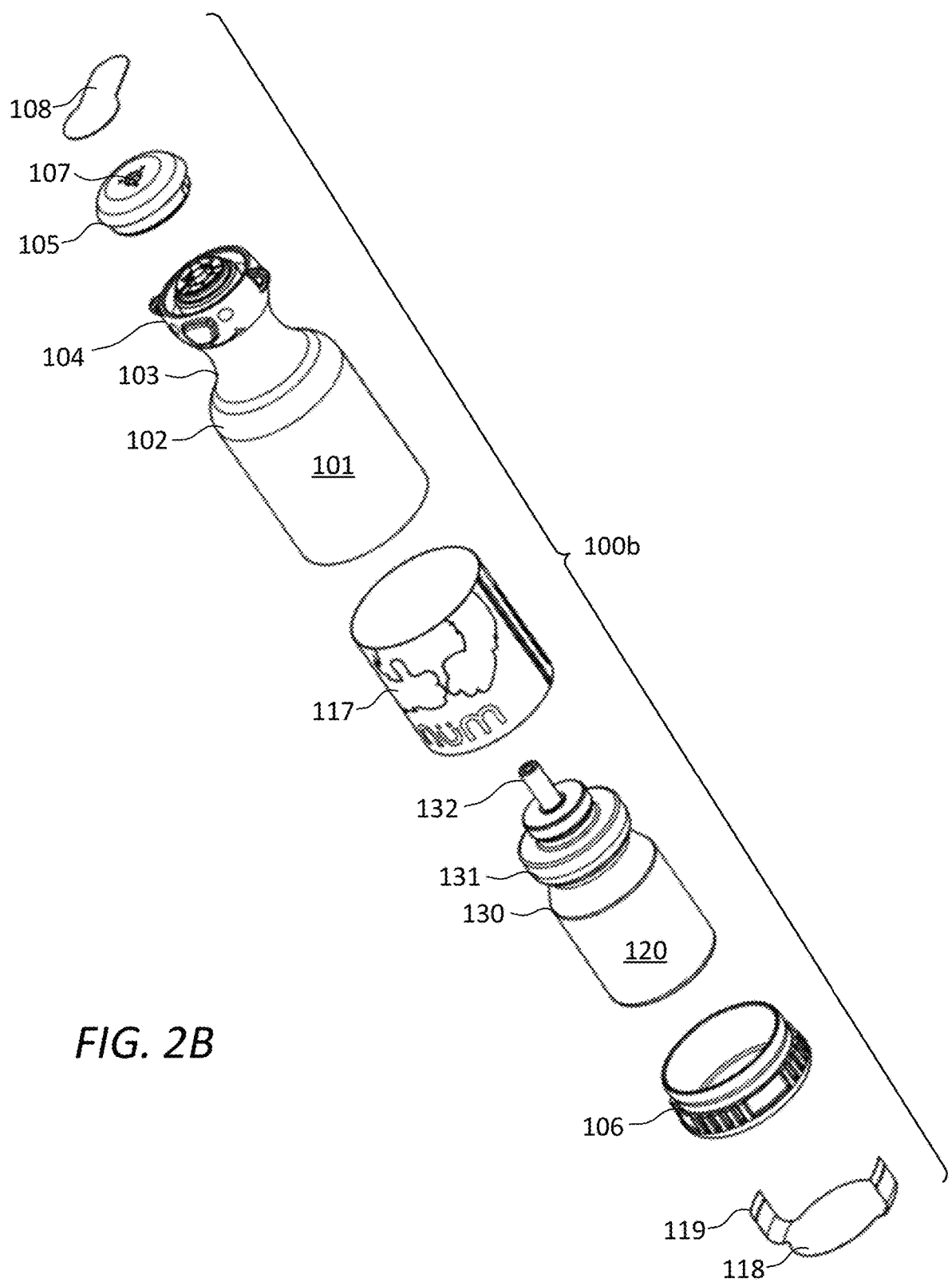
FIG. 2B illustrates an exploded view of the dispenser of FIG. 1B according to the present disclosure.

With reference to FIGS. 1A-1B, and exploded views 2A, 2B an embodiment of a dispenser is generally designated by the reference numeral 100a, 100b (hereinafter collectively also referred to by callout 100), depicted as having an elongated housing 101a, 101b, (hereinafter collectively also referred to by callout 101). In one aspect, the housing 101 is generally cylindrical. Housing 101 comprises shoulder 102 and adjacent taper portion 103 having an inward/outward taper in proximity to a distal end, a dispensing end 104 with lid 105 adjacent to the distal end, the dispensing end 104 and lid 105 configured for coupling together. Taper 103 is configured to allow for comfortable and secure interaction with of a pair of human digits, for example the index and ring finger, and thus, can provide for one-handed operation when coupled with the thumb as described herein.

Proximal end of housing 101 includes a bottom cover 106 configured for coupling with housing 101 and designed with a sealing interface to preserve fluid path sterility. Removable pull-tab 108 is reversibly sealed to lid 105 and hermetically covers opening 107 and vent holes 129 preventing contamination and preserving fluid path sterility. Pull-tab 108 covering also preserves the sterility of all area inside of the seal to lid 105, ensuring that surfaces proximate to the spray opening 107 remain sterile until use. Pull tab 108 may be Tyvek. Thus, the fluid path sterility for the dispenser 100 is preserved during shipping and up to the point of use with a combination of the bottom cover 106, and the air permeable, sterile barrier pull tab 108.

Figure 14:
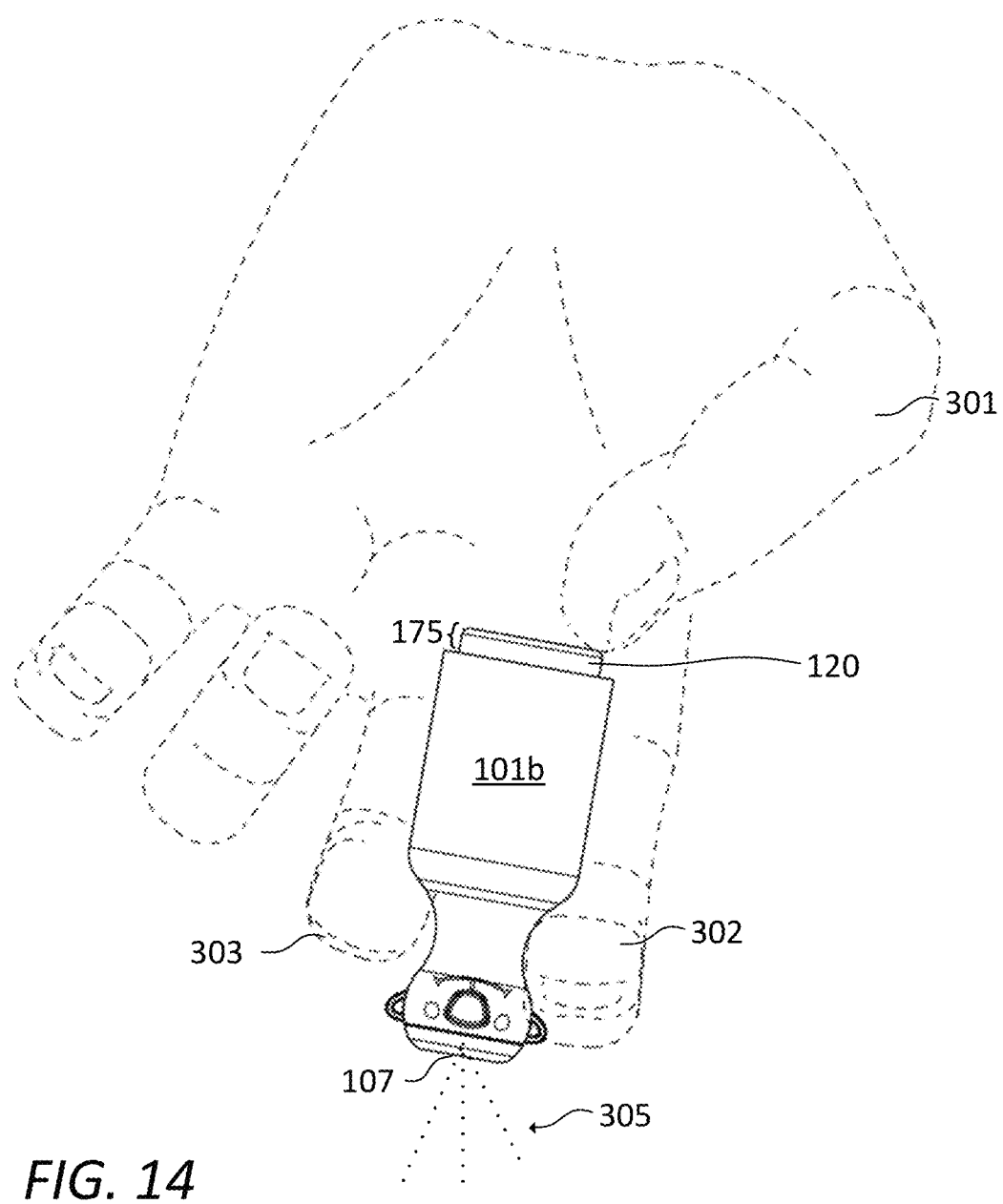
FIG. 14 is perspective view of the dispenser of the invention illustrating an exemplary use of the device as disclosed and described herein.

Proximal end of housing 101 receives a majority of vapocoolant container 120 that contains, e.g., vapocoolant. A remainder portion 175 (FIG. 14) of the container 120 extends from the housing 101. Container 120 includes shoulder 130 adjacent tapered neck adjacent distal end 131 with nozzle 132 projecting therefrom. In one example, the contents of the container 120 are under pressure such that the pressure inside of the container 120 is greater than the ambient pressure. Alternate dispenser 100b includes optional projections from the distal end and/or dispensing end 104 so as to present an appealing, friendly, animal-like appearance, for example, a "teddy bear" with a pair of ears 110 and nose 112 for use in pediatrics.

Tamper evident seal 118 with extensions 119 drape over the side of cover 106 potentially preventing contamination associated with dislodgement of cover 106 and can also provide for a visual indication of sterility for the end user. An optional cylindrical label 117 is sized to surround circumference of housing 101 in some embodiments providing additional security to tamper evident seal extensions 119 by additionally affixing the seal extensions 119 to housing 101. In one example, label 117 comprises artwork or other indicia complimenting optional projections 110 and 112. In yet other example, label 117 comprises an integrated bandage or a sticker for use with pediatric patients.

In one example, the combination of tamper evident seal 118 and cover 106 functions cooperatively to retain the container in the housing and isolates the interior of the housing from the ambient environment, thus improving and/or maintaining sterility after sterilization of the dispenser 100. Because nozzle 132 of container 120 may or may not seal completely with the channel 135b of the housing 101, entrapped air within the housing of the device can vent through the existing opening 107 in the absence of hermetic seal of pull tab 108. In one example, in order to keep the fluid path of the vapocoolant sterile within the dispenser until use, the presently disclosed dispenser 100 implements improved design elements. In one example, the vapocoolant is kept sterile, as well as all surfaces on the vapocoolant container 120, all internal surfaces of the housing 101, internal surfaces of bottom cover 106, and the region bounded by the pull tab 108 and lid 105, e.g., pull tab 108 creates a peelable, hermetic seal. The bottom cover 106 creates a microbial barrier with housing 101, by creating an annual hermetic seal between the bottom cover 106 and the body of the housing 101. In an alternative design, housing 101-bottom cover 106 microbial barrier can be configured to include a tortuous path, rather than a hermetic seal.

In one example, dispenser 100, pull tab 108 and lid 105 utilizes a breathable, sterile barrier material (e.g., Tyvek), which in addition to preventing the ingress of microbial contaminants, permits the interior of the device to remain at ambient pressure through vent holes 129, and prevents changes in barometric pressure or temperature, e.g., from popping off the bottom cover 106, due to the breathability of pull tab 108. In another example, pull tab 108 could be replaced with another element such as a cap or non-breathable element.

In the presently disclosed dispenser 100, two design configurations are possible to maintain the sterile fluid pathway of the system. In a first example, either or both of the pull tab 108-lid 105 mating junction or bottom cover 106-housing 101 mating junction are configured to provide a sterile barrier and/or provide a tortuous path. In a second both the pull tab 108-lid 105 mating junction and bottom cover 106-housing 101 mating junction are hermetically and non-breathably sealed but are otherwise capable of preventing changes in pressure from rupturing the hermetic seal.

The presently disclosed dispenser 100 in one example is configured so that the pull tab 108-lid 105 and bottom cover 106-housing 101 configuration both essentially provide sterile barrier junctions so as to maintain sterility of dispenser 100, e.g., even if the dispenser are carried around in pockets of clinicians, etc., prior to use.

FIGS. 3A and 4A depict orthogonal views of the dispenser 100, with FIGS. 3B and 4B providing corresponding section views along section line 3B-3B and 4B-4B, respectively. Housing 101 includes nozzle receiving members 133 with channel 135b essentially centered along the longitudinal axis 3B-3B of the housing 101. As shown in FIG. 3C, depicting enlarged view of section 3C of FIG. 3B, nozzle receiving members 133 includes shoulder 137 configured for engaging nozzle 132 of container 120 in a first state prior to activation/release of vapocoolant via opening 232 of valve member 136 and aligns distal conduit 135a of nozzle 132 with channel 135b of housing. Channel 135b fluidically couples with opening 107 of lid 105. Distal conduit 135a is cooperatively engaged with valve member 136 which is held under the pressure of the contents of container 120 in a closed position in the first state prior to activation. Valve member 136 can be a press-down valve or other suitable valve for releasing pressurized contents.

Displacement of valve member 136 along longitudinal axis 3B-3B in a second state or activation state, allows pressurized contents of container 120 to enter channel 135 for release through opening 107. Projections 124 from inner surface of housing 101 are positioned between shoulder 130 and distal end 131 of container 120 securing container in housing when support afforded by bottom cover 106 is removed. Interior of housing 101 adjacent to taper 103 provides for a predetermined reversible longitudinal travel distance of the distal end 131 of container 120 within the housing 101 during transition from the first state to the activation state sufficient for displacement of valve member 136 and the release of vapocoolant.

Inner diameter of lid 105 is sized for receiving by housing 101 and provides for hermetic sealing, for example, by ultrasonic, sonic welding, or adhesive, such that lid 105 forms an airtight, sterile seal with housing 101. Inner surface of housing 101 includes inwardly projecting protrusions 123 which prevent unintentional longitudinal movement of container 120 within housing towards bottom cover 106 while in the first state.

Bottom cover 106 has annular ring 174 configured to be received by the annular region 101c of housing 101. The annular ring 174 and annular region 101a can be sized for an interference fit which provides a sterile barrier seal. Additional sealing elements can be employed, such as o-rings or sealing compounds. The housing 101 may also employ locking features 125 that engage below the annular ring 174 to provide additional securement for the bottom cover 106. Bottom cover 106 can include inwardly projecting protrusion 173 to securely position container 120 in the interior of housing 101 and maintain alignment or fitment of nozzle receiving members 133 with nozzle 132.

Figure 5:
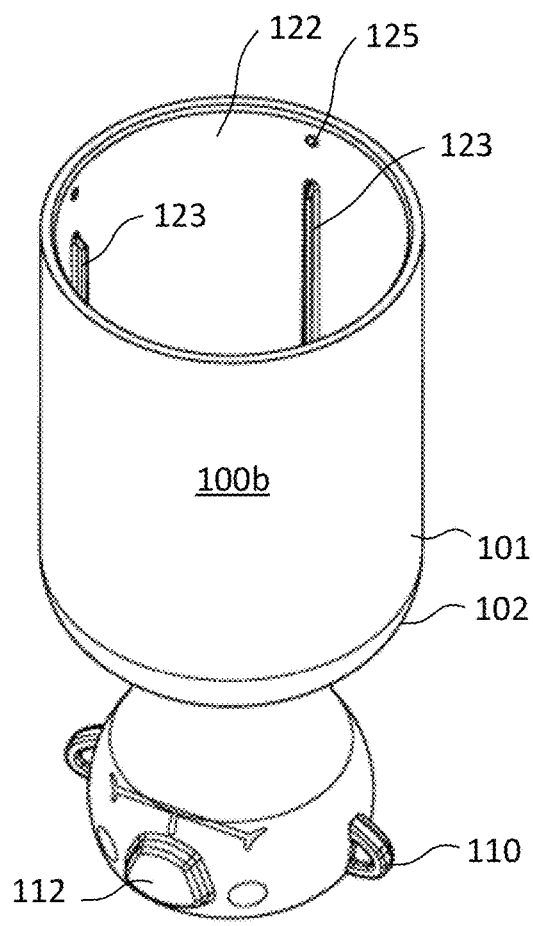
FIG. 5 is a bottom perspective view of the dispenser of FIG. 1B.
Figure 6:
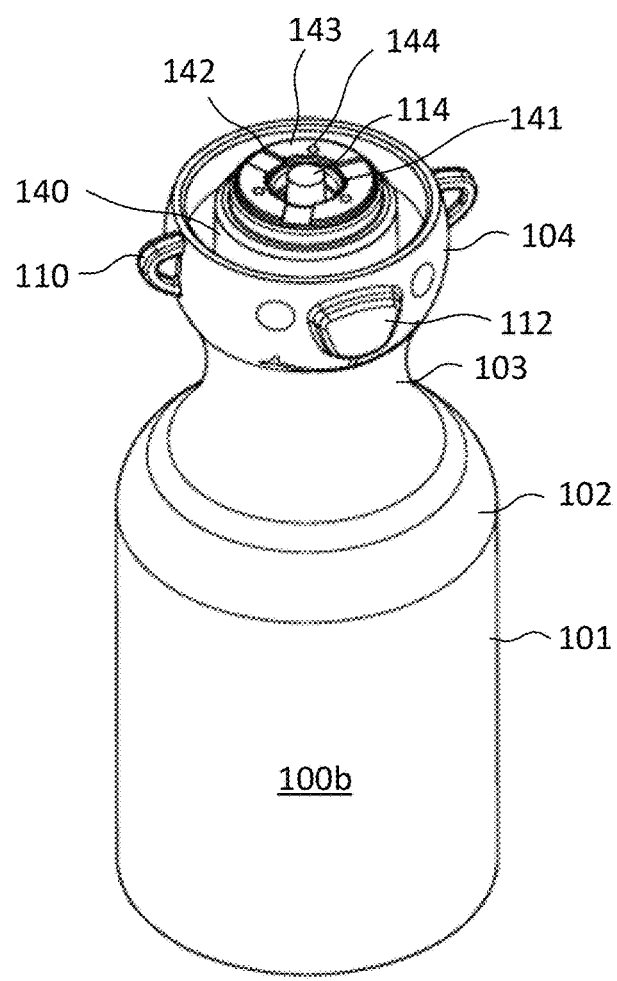
FIG. 6 is a top perspective view of the dispenser of FIG. 1B.

FIGS. 5 and 6 depict perspective bottom and top views, respectively, of the housing 101 with the container 120, bottom cover 106, and lid 105 removed. Interior inner surface 122 of housing 101 includes a plurality of spaced-apart longitudinally-extending projections 123 which can function to guide container 120 upon assembly to prevent discharge of container 120. Additionally, inwardly tapered extending projections 123 can provide a predetermined resistance of longitudinal motion of the container 120 and the subsequent activation of valve member 136 by the user. Longitudinally extending projections 123 can vary in extension into the interior of housing 101, for example, a longitudinal taper.

Distal portion 104 encircles projecting annular platform 140 terminating in dispensing assembly 141. Annular ring 143 of dispensing assembly 141 encircles post 114. Annular ring 143 includes a plurality of spaced apart cutouts 142 on exposed surface of annular ring 143.

Figure 7A:
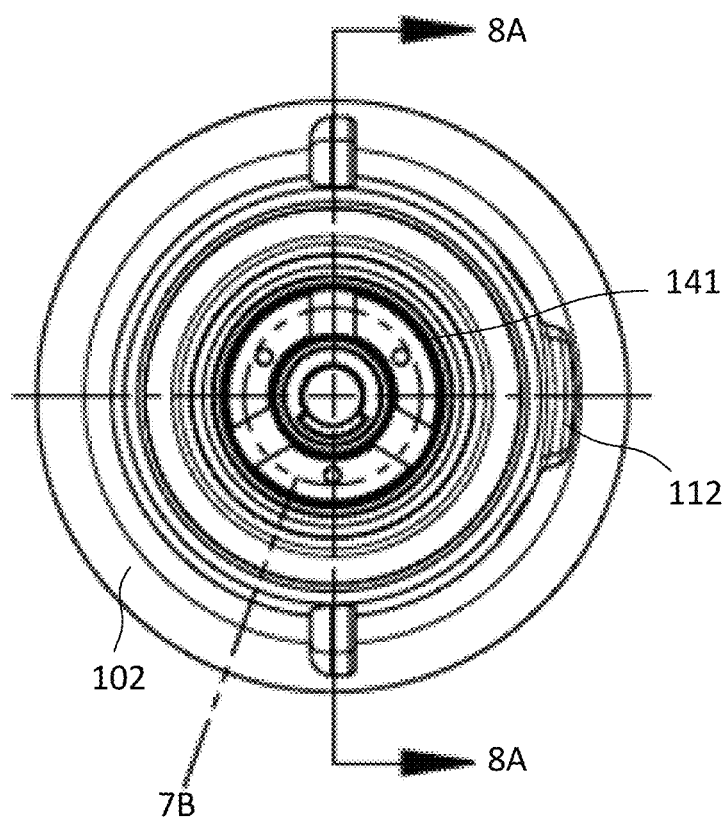
FIG. 7A is a top plan view of the housing of the dispenser of FIG. 6.
Figure 7B:
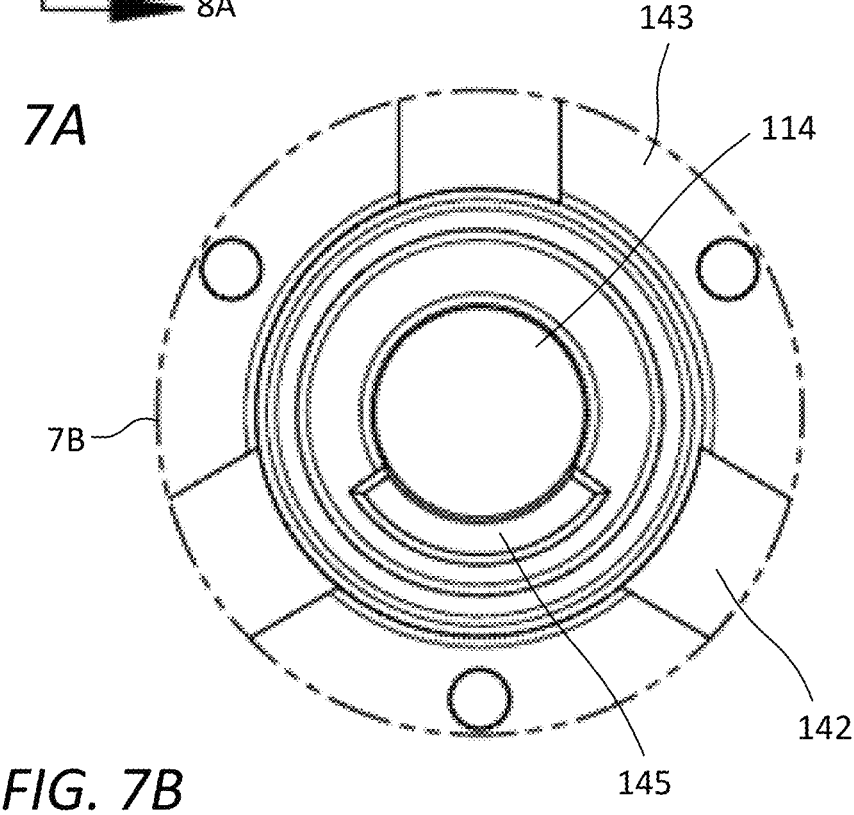
FIG. 7B is an enlarged view of section 7B of FIG. 7A.
Figure 8A:
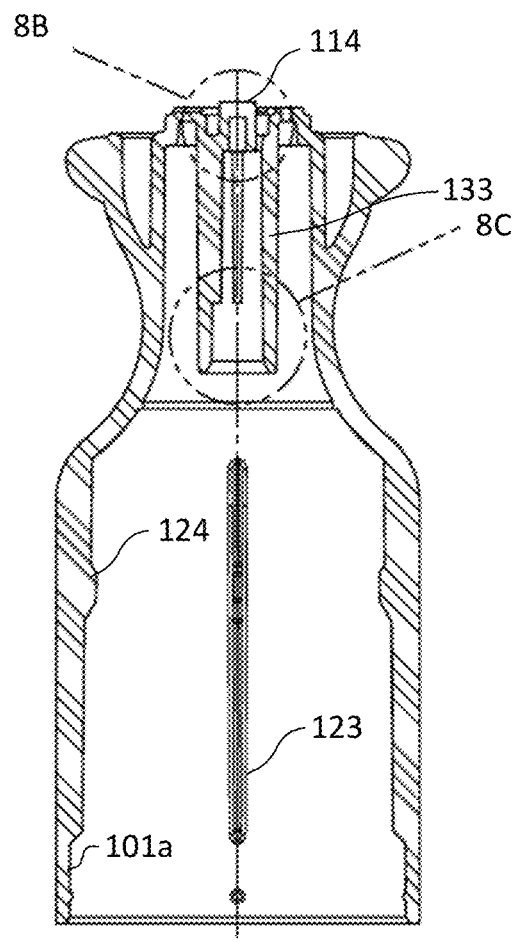
FIG. 8A is a section view of the dispenser of FIG. 6.
Figure 8B:
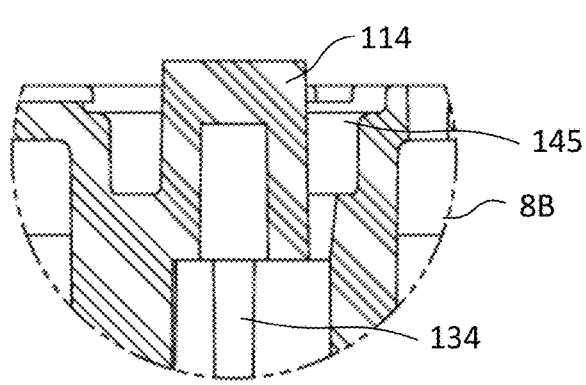
FIG. 8B is an enlarged view of section 8B of FIG. 8A.
Figure 8C:
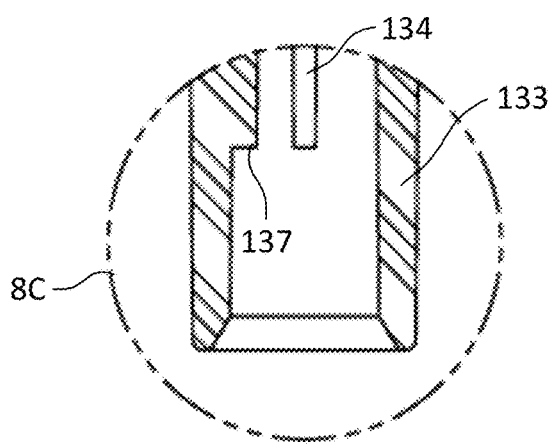
FIG. 8C is an enlarged view of section 8C of FIG. 8A.

FIGS. 7A and 7B depict a top plan view of distal portion 104 an enlarged view of dispensing assembly 141. FIGS. 8A, 8B, and 8C provide a sectional view and enlarged views of dispensing assembly 141. As shown, opening 145 fluidically coupled to conduit 134 partially encircles post 114 and provides for a fluidic path of the contents of container 120 of dispenser 100 when in the activated state.

Figure 9A:
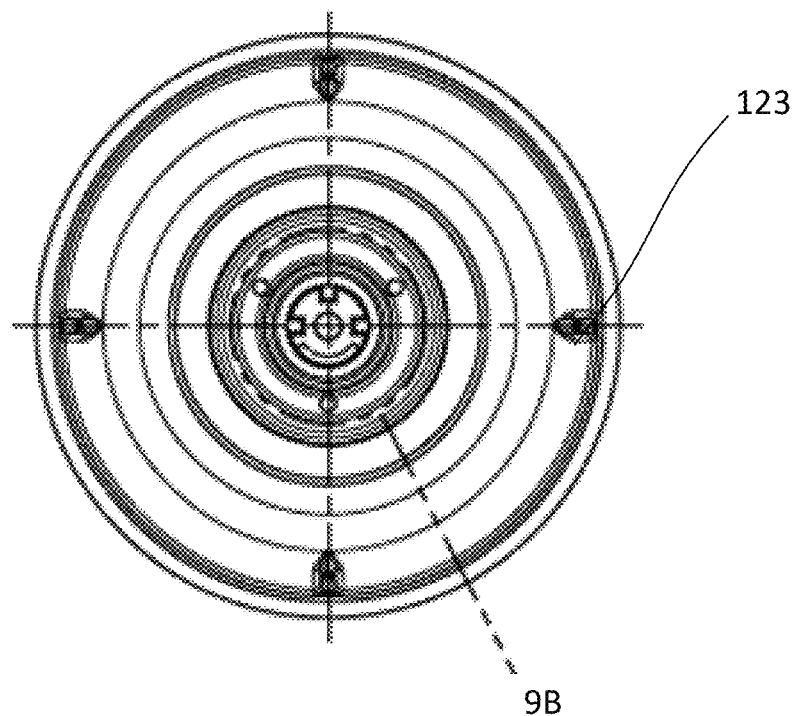
FIG. 9A is a bottom plan view of the housing of the dispenser of FIG. 6.
Figure 9B:
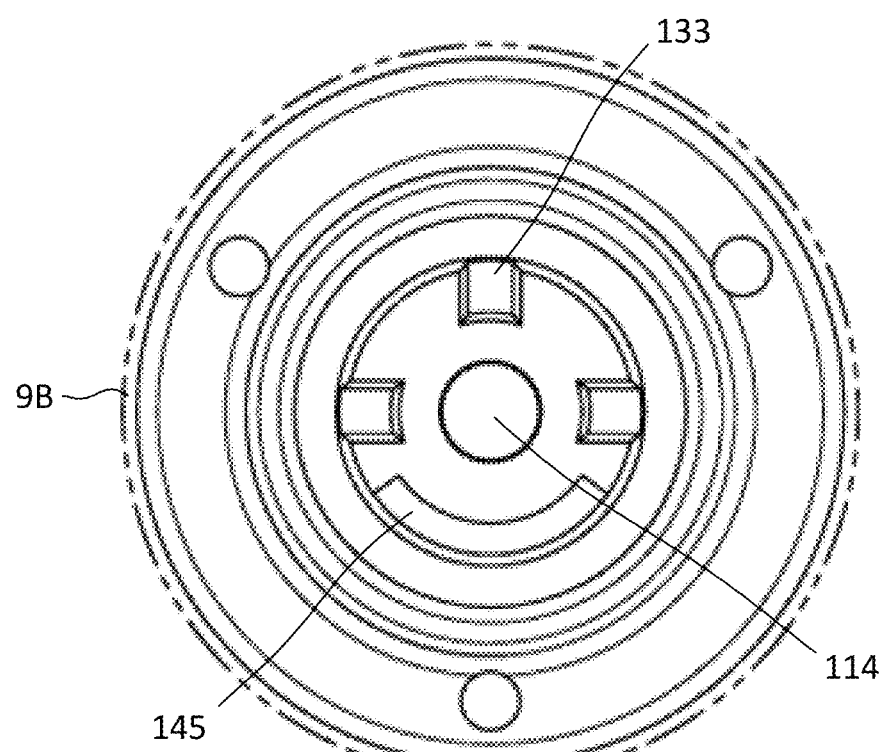
FIG. 9B is an enlarged view of section 9B of FIG. 9A.
Figure 10:
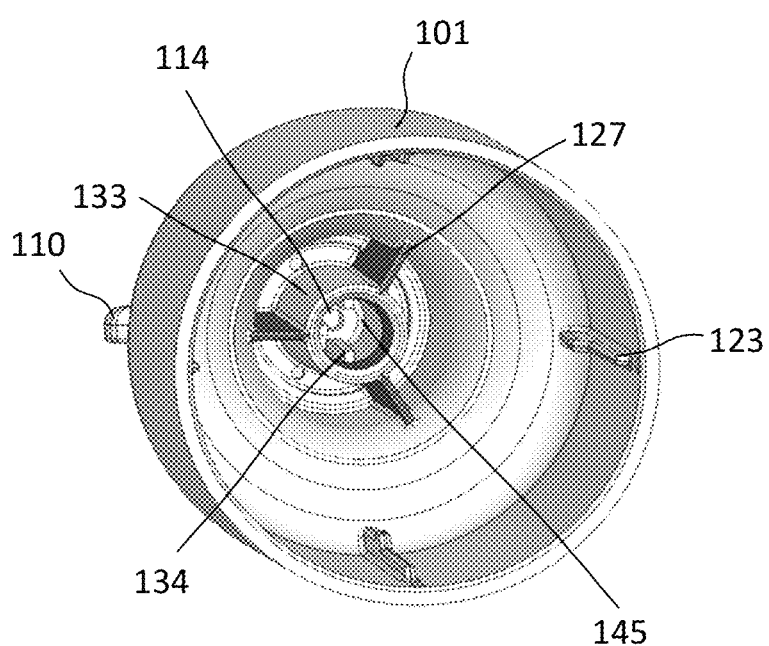
FIG. 10 is a perspective bottom view of an alternate housing of the dispenser device disclosed and described herein.

FIGS. 9A and 9B depict a bottom plan view of housing and enlarged section 9B of FIG. 9A showing nozzle receiving member 133, post 114, and opening 145. FIG. 10 depicts an alternate embodiment of housing 101 whereby nozzle receiving members 133 is radiantly supported by a plurality of supporting walls 127.

Figure 11A:
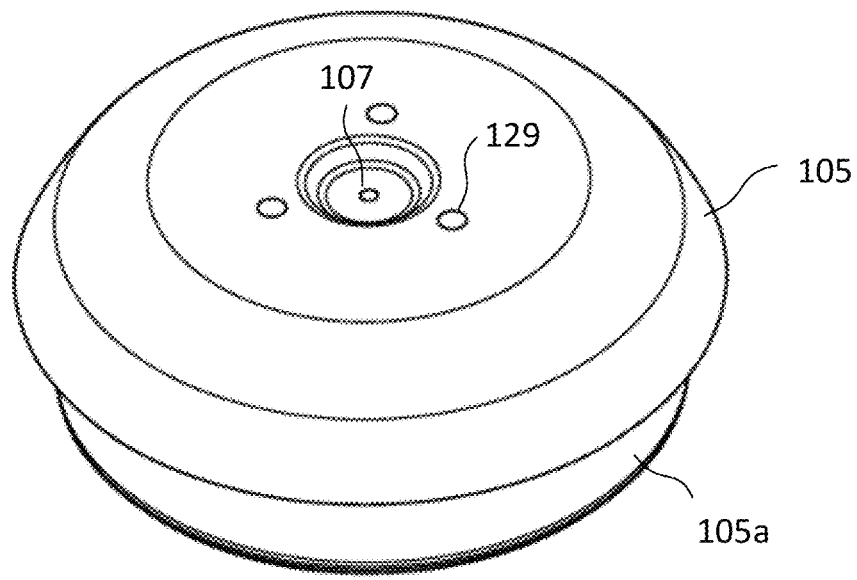
FIGS. 11A and 11B are top and bottom perspective views, respectively, of a bottom cover of the dispenser disclosed and described herein.
Figure 11B:
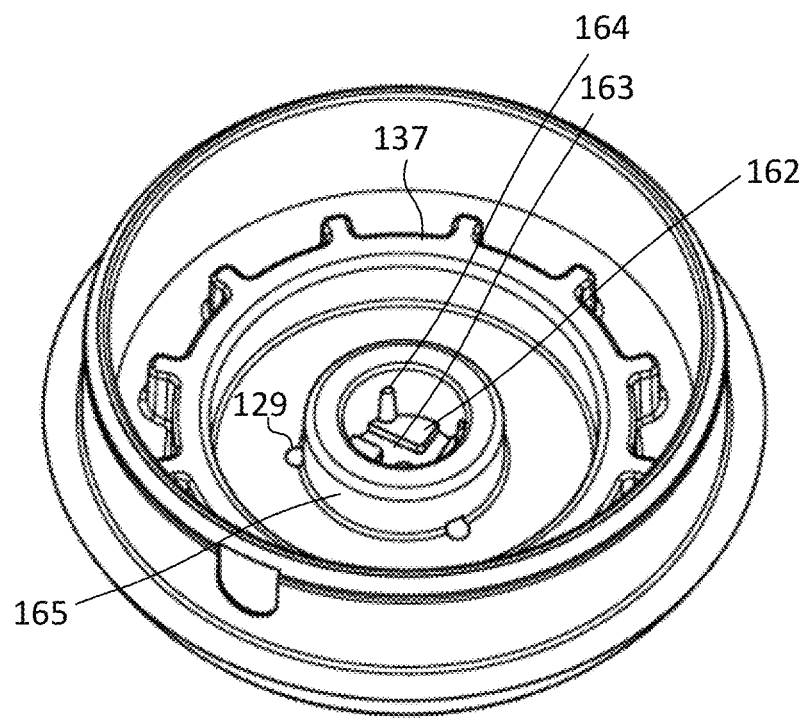
Figure 11C:
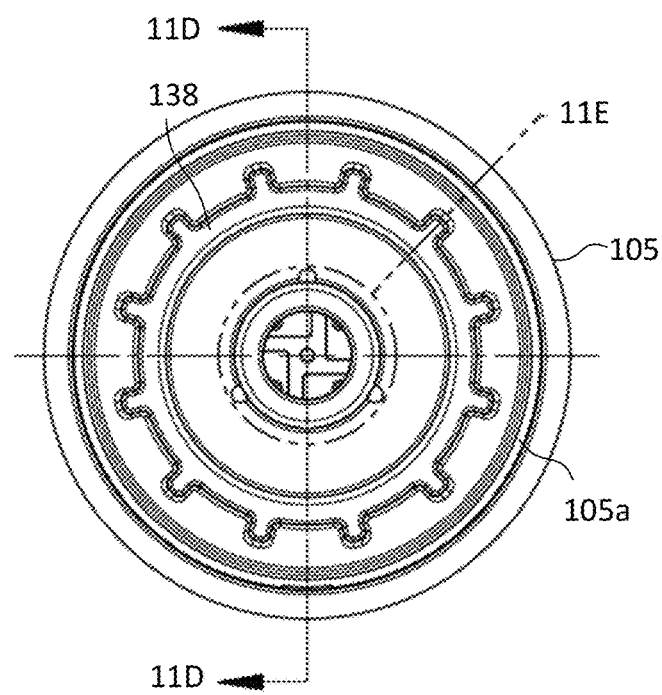
FIG. 11C is a bottom plan view of the cover of FIG. 11A.
Figure 11D:
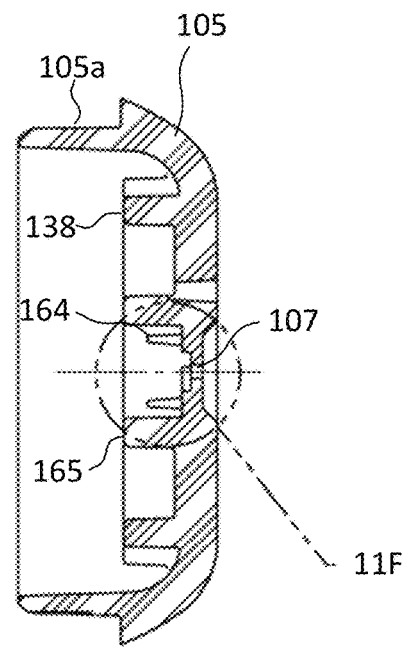
FIG. 11D is a section view along section line 11D-11D of FIG. 11C.
Figure 11E:
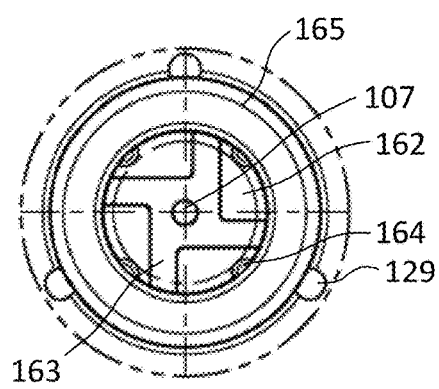
FIG. 11E is an enlarged view of section 11E of FIG. 11C.
Figure 11F:
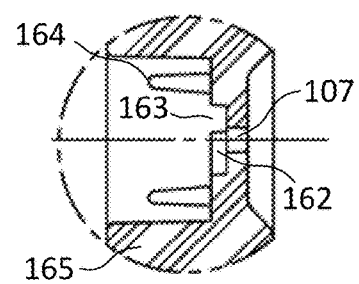
FIG. 11F is an enlarged view of section 11F of FIG. 11D

FIGS. 11A and 11B depict top and bottom perspective views of lid 105. FIG. 11C depicts a plan view of the underside of lid 105. FIG. 11D is a sectional view along line 11D-11D. FIG. 11E is an enlarged view of section 11E of FIG. 11D, and FIG. 11F is an enlarged view of section 11F of FIG. 11E. Lid 105 includes reduced diameter annular ring 105a sized to encircle annular platform 140, for example in an interference fit relationship or may loosely fit for subsequent ultrasonic welding. Top surface of lid includes vent holes 129 surrounding opening 107. Vent holes 129 provide a pathway for pressure equalization of the internal volume of the housing, preventing pressure build up and dislodgment of bottom cover 106 and pull tab 108 preserving the sterile fluid path. Vent holes may also provide for outgassing during sterilization using high-energy radiation such as x-rays, gamma rays, or electron-beam as well as maintaining pressure equilibrium during transportation/storage and temperature changes. Pull tab 108 is made of an air permeable sterile barrier material (e.g. Tyvek) and is continuously sealed around vent holes 129 and opening 107. Interior surface of lid 105 includes projecting annular wheel 138 and annular protrusion 165 providing two annular welds when joined to the distal portion 104 of housing 101. Annular wheel 138 encircles annular protrusion 165 sized to encircle post 114. Raised platform 162 having projecting posts defines channels 163 when lid 105 is joined to the housing 101 and brought in contact with the distal surface of post 114, a dispenser "spray nozzle" is formed, providing for efficient diffusion of escaping contents of container 120 and working cooperatively with opening 145 for efficient and even dispensing of vapocoolant. In one example, the aforementioned components of lid 105 comprise a micromist assembly configured to split the flow of the vapocoolant upon release from the container 120 so that one or more flows of vapocoolant can recombine in and/or interact with one or more components of lid 105 so as to provide a vortex that aids in making a finer mist of vapocoolant.

Figures 12A, 12B:
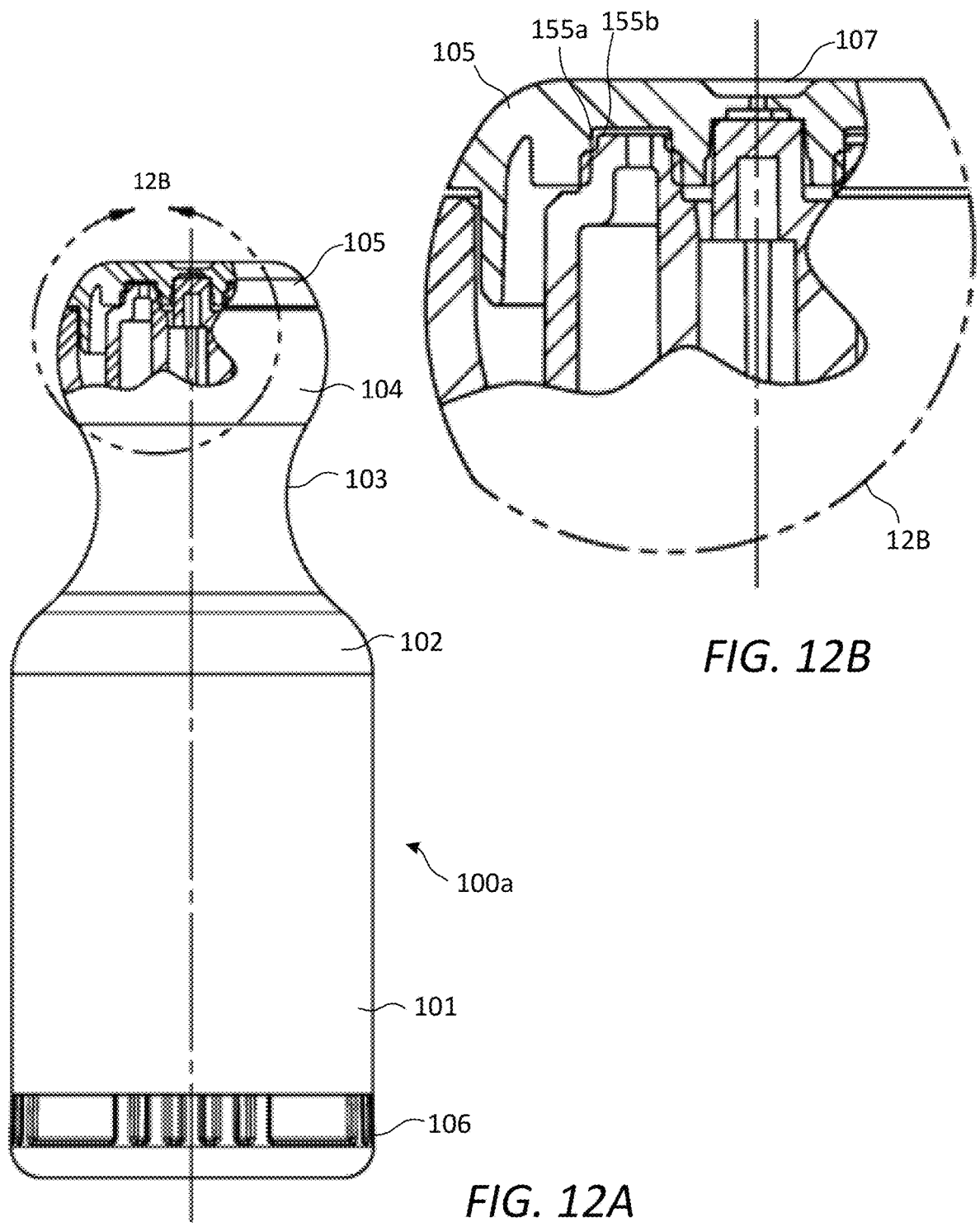
FIG. 12A is a partial cutaway perspective side view of the dispenser of FIG. 1A.
FIG. 12B is an enlarged view of section 12B of FIG. 12A.

FIG. 12A depicts a partial section view of the housing 101 and lid 105 joining. FIG. 12B is an enlarged view of section 12B of FIG. 12A showing various ultrasonic welding spots 155a, 155b complementarily positioned among lid 105 and distal portion 104 of housing 101 for hermetically sealing lid 105 to distal portion 104 of housing 101. Welds 155a, 155b provide for the formation of a space above annular ring 143 on housing 101 and the inside of lid 105, the space fluidly communicates with the vent holes 129 and vent holes 144 of housing 101, allowing the interior of the dispenser to vent to the outside environment through the sterile barrier pull tab 108 that is sealed around the vent holes 129 on the external surface of lid 105.

Figure 13A:
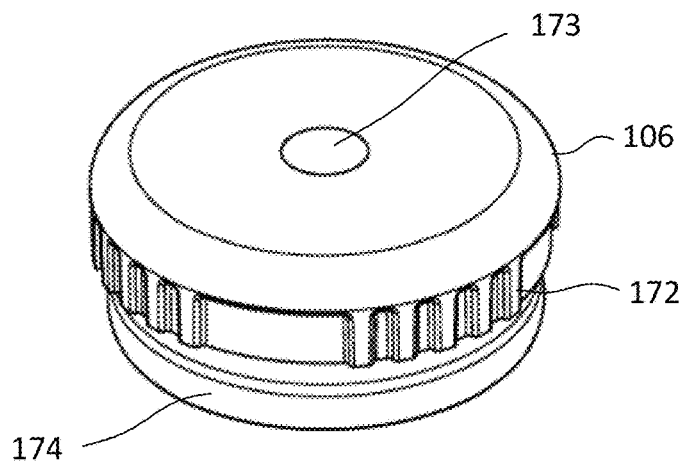
FIG. 13A is a top perspective view of the bottom cover of the dispenser disclosed and described herein.
Figure 13B:
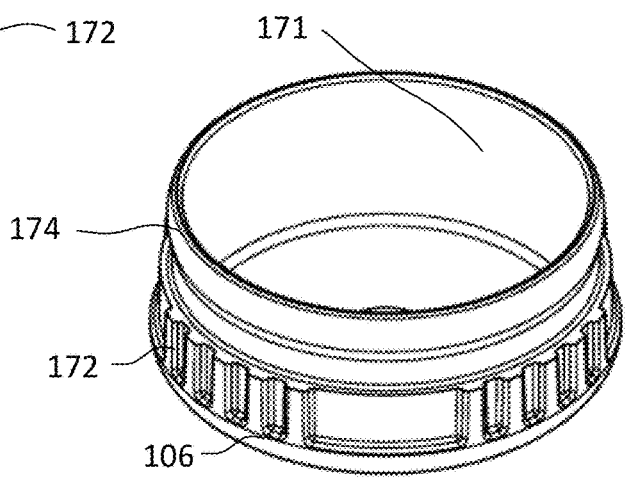
FIG. 13B is a bottom perspective view of the bottom cover of the dispenser disclosed and described herein.
Figure 13C:
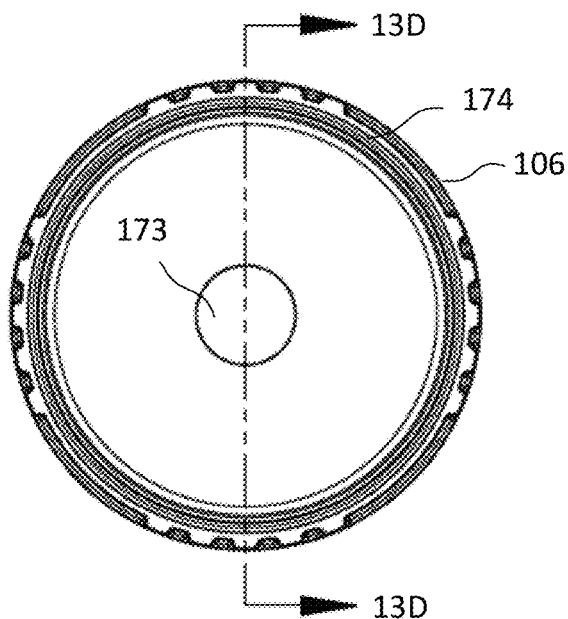
FIG. 13C is a top plan view of the bottom cover of the dispenser disclosed and described herein.
Figure 13D:
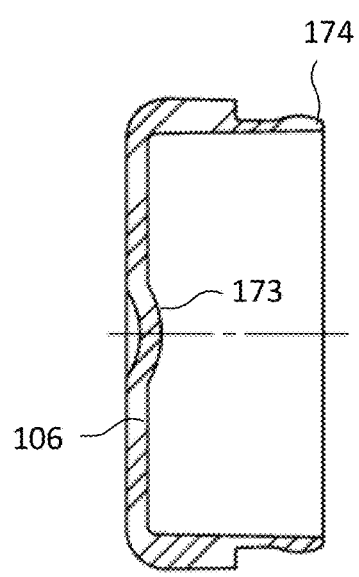
FIG. 13D is a section view along section line 13D-13D of FIG. 13C.

FIG. 13A depicts a perspective view of bottom cover 106 having ergonomic features 172 for assisting in removing cover from housing 101. Bottom cover 106 includes smaller diameter annular ring 174 for engaging annular region 101a. FIG. 13B depicts a perspective view of bottom cover 106 showing surface 171. FIG. 13C depicts a top plan view of inner surface of the bottom cover 106 showing protrusion 173. FIG. 13D is a section view along section line 13D-13D of FIG. 13C. In one variation, the container 120 is not refillable and dispenser 100 is intended for single use. In another example, dispenser 100 is configured to be used at least once or until depleted of contents, the dispenser 100 would then be disposable.

With the various embodiments having been described in detail above, a method of operation will now be explained. Container 120 has vapocoolant contained therein by valve member 136, e.g., tilt-valve, press-valve, with nozzle 132 received by a plurality of nozzle receiving members 133, which is shown as three members integral with housing 101. The fixed relationship between the interval nozzle receiving members 133 of the housing and the nozzle 132 of valve member 136 provides, in a first state, a sealed relationship of the container and allows transition to a second state where the nozzle 132 of container 120 is urged towards the nozzle receiving members 133 of the housing (via linear translation of the container into the housing along the longitudinal axis housing by the user's thumb, for example) causing the nozzle 132 to engage the nozzle receiving members 133 allowing release of the vapocoolant essentially parallel with the longitudinal axis of housing 101. This guides the escaping vapocoolant perpendicularly towards raised platform 162 and channels 163 and ultimately exiting via opening 145. When the user releases the force on the container, the valve member 136, alone or in combination with inwardly projecting protrusions 123, provides a restoring force to translate the container in the opposite direction, disengaging the nozzle 132 from nozzle receiving member and back to the first state while also discontinuing dispensing of the vapocoolant.

In one aspect, peel away tamper evident seal 118 and tab 108 is removed. Alternatively, the entire bottom cover assembly 106 can be removed together with tamper evident seal 118. With bottom cover 106 removed, portion of container 120 is exposed from housing 101. In one example, as shown, a user may grasp the tapered portion of housing 101 between index finger 302 and ring finger 303 and position thumb 301 against container 120. Exerting a force on container 120 using thumb 301 translates container longitudinally within housing 101 and places device and an activated state whereby valve member 136 is actuated releasing the contents 305 of container 120 through opening 107 thus, the present dispenser 100 avoids needing a "second hand" and the need to put dispenser 100 down so as to access and use another device. In one example, a user may grasp the tapered portion of housing 101 between index finger 302 and ring finger 303 and position thumb 301 against container 120 so as to use the dispenser 100 in a one-handed, "pen-like" or "air-brush-like" manner.

Figure 15:
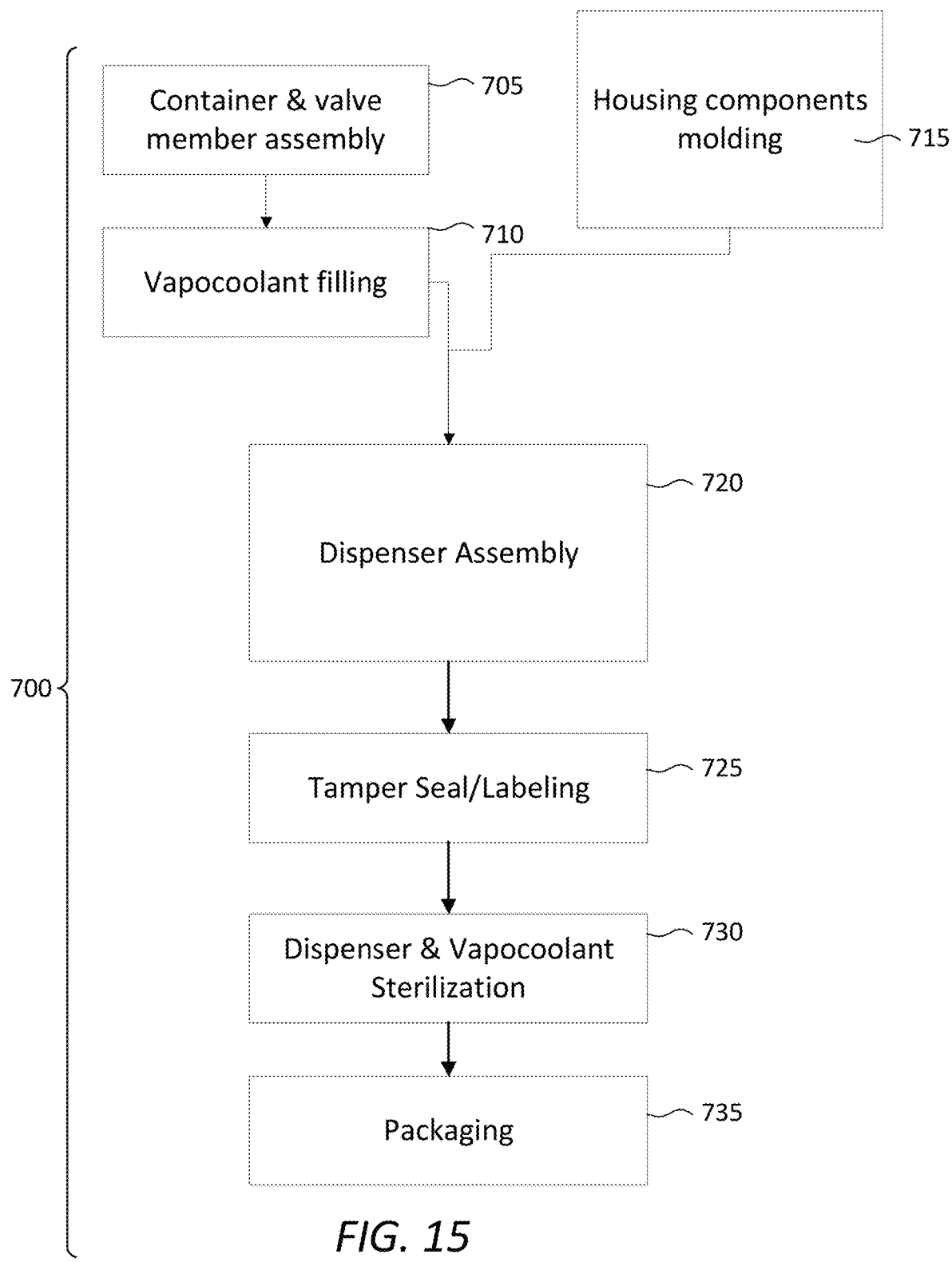
FIG. 15 is a flowchart depicting an assembly process of the dispenser as disclosed and described herein.

Referring to FIG. 15, a packaging method providing for aseptic or semi-aseptic assembly is depicted by flowchart 700. Step 705 includes container 120 and valve member 136 assembly and vapocoolant filling step 710. Independently, or concurrently, housing components, typically via injection molding or other thermoplastic molding technique are used to construct housing 101, lid 105, and bottom cover 106 as depicted in step 715. Step 720 brings housing 101 and container 120 together for device assembly. Step 720 can be performed in a sterile environment, clean room environment, or under other aseptic or semi-aseptic conditions and includes, for example, lid 105 welding to housing 101, heat sealing of pull tab 108 to lid 105, introducing container 120 to housing 101, and press attachment of bottom cover 106 to housing. Likewise, step 725 involves applying the tamper seal and/or optional labeling. Step 730 involves dispenser 100 sterilization using high energy radiation so as to sterilize the vapocoolant contents of container 120 as well as dispenser 100. Step 735 involves packaging of the nonsterile and hermetically sealed dispenser 100.

In one aspect, the dispenser 100 can be configured to release vapocoolant for a time of approximately 1 to 10 seconds, or longer. In one aspect the dispenser is configured to release vapocoolant for 1-2 seconds, 3 to 5 seconds, 6-10 seconds, or longer. In other aspects, the dispenser 100 is configured to release vapocoolant continuously.

Either while the vapocoolant is flowing or just after the flow of the vapocoolant is stopped, the skin can then be accessed e.g., penetrated by a needle of the syringe to a desired depth, insertion of catheter or other medical device or the like. In using the dispenser 100 disclosed, various types of dermal/sub-dermal accesses may be subsequently employed, such as subcutaneous, intramuscular or intradermal.

If desired, additional injections may be carried out at the same or at different locations. During the process of injection multiple injections at the same or different sites, additional vapocoolant may be dispensed as desired to provide or maintain the numbness of the skin at that location. In one example, dispenser 100 can be optionally packaged before sterilization. Thus, in one example, a secondary packaging configuration is employed comprising shipper boxes arranged so that each packaged dispenser is in a single layer so as to complement the low-penetration properties of e-beam radiation and avoid a multi-layered packaged device system would otherwise require a higher maximum dosage to obtain the requisite sterility than the envisioned single-layered packaging. Reducing the maximum dose of radiation for product sterilization reduces radiation damage to components, e.g., valve member 136 of container 120.

The devices and assemblies presently described provide for a configuration and function that is advantageous for a person in need of numbing an injection site prior to self-injection, for pediatrics, or for example, injections in proximity to the buttocks or other locations such as the lower legs, back, shoulders, etc.

As such, in this way, the present disclosure provides an effective way of dispensing a vapocoolant onto the skin of a patient, e.g., that would benefit from the anesthetic effect of a vapocoolant and/or where a medical treatment is to take place that would benefit from the anesthetic effect of a vapocoolant, so that an injection or other invasive procedure is painless or less painful. The present disclosure is not limited for use in association with injections for aesthetic enhancement. Rather, it may be used in combination with any invasive procedure and/or with other medical devices, or for use with an injector, catheter, inserter, or other medical device that is invasive and likely to result in pain to the patient.

We claim:

1. A sterilizable vapocoolant dispenser, comprising:
   a container comprising vapocoolant, the container having a valve member configured to release the vapocoolant;
   a housing having a distal open end; a proximal open end sized to receive a majority portion of the container and exposing a remainder portion of the container;
   a bottom cover sealing the proximal open end and the remainder portion of the container;
   a lid sealing the distal open end, the lid coupled to the valve member; and
   a nozzle receiving member positioned in the housing and configured to engage the valve member for releasing the vapocoolant;
   wherein the container and its contents are configured for sterilization by high energy radiation.

2. The sterilizable vapocoolant dispenser of claim 1, wherein the housing has an inward and outward tapered portion between the distal open end and the proximal open end for receiving fingers of a human hand.

3. The sterilizable vapocoolant dispenser of claim 1, wherein the container is fixedly positioned in the housing.

4. The sterilizable vapocoolant dispenser of claim 1, wherein the lid is irreversibly sealed to the distal open end.

5. The sterilizable vapocoolant dispenser of claim 1, wherein the bottom cover is releasably coupled to the proximal open end.

6. A sterilized vapocoolant dispenser, comprising:
   a container comprising sterilized vapocoolant, the container having a valve member configured to release the vapocoolant;
   a housing having a distal open end; a proximal open end sized to receive a majority portion of the container and exposing the remainder portion of the container, and;
   a bottom cover sealing the proximal open end and the remainder portion of the container;
   a lid sealing the distal open end, the lid coupled to the valve member; and
   a nozzle receiving member positioned in the housing and configured to engage the valve member for releasing the vapocoolant;
   wherein the container and vapocoolant are configured to remain sterilized until used.

7. The sterilizable vapocoolant dispenser of claim 6, wherein the container is fixedly positioned in the housing.

8. The sterilizable vapocoolant dispenser of claim 6, wherein the lid is irreversibly sealed to the distal open end.

9. The sterilizable vapocoolant dispenser of claim 6, wherein the bottom cover is releasably coupled to the proximal open end.

10. A method of manufacturing a sterilized vapocoolant dispenser, the method comprising:
    introducing a container containing vapocoolant to a housing, the housing comprising a distal open end, and a proximal open end sized to receive a majority portion of the container and exposing the remainder portion of the container;
    sealing the proximal open end and the remainder portion of the container with a releasably sealed bottom cover;
    sealing the distal open end with an irreversibly sealed lid; and
    sterilizing the vapocoolant and housing simultaneously using high energy radiation.

* * * * *